(12) United States Patent
Lupotti et al.

(10) Patent No.: US 11,707,231 B2
(45) Date of Patent: Jul. 25, 2023

(54) APPARATUSES, METHODS, AND SYSTEMS FOR CONTACT FORCE SENSING

(71) Applicant: St. Jude Medical International Holding S.á r.l., Luxembourg (LU)

(72) Inventors: Fermin A. Lupotti, Lake Forest, CA (US); Arthur G. Blanck, Ramona, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 889 days.

(21) Appl. No.: 16/492,208

(22) PCT Filed: Mar. 9, 2018

(86) PCT No.: PCT/IB2018/051577
§ 371 (c)(1),
(2) Date: Sep. 9, 2019

(87) PCT Pub. No.: WO2018/163129
PCT Pub. Date: Sep. 13, 2018

(65) Prior Publication Data
US 2020/0008747 A1    Jan. 9, 2020

Related U.S. Application Data

(60) Provisional application No. 62/469,572, filed on Mar. 10, 2017.

(51) Int. Cl.
*A61B 5/00*     (2006.01)
*A61B 18/14*    (2006.01)
(Continued)

(52) U.S. Cl.
CPC ............ *A61B 5/6885* (2013.01); *A61B 5/287* (2021.01); *A61B 5/6852* (2013.01);
(Continued)

(58) Field of Classification Search
CPC ..... A61B 5/6885; A61B 5/287; A61B 5/6852; A61B 18/1492; A61B 2018/00351;
(Continued)

(56) References Cited

U.S. PATENT DOCUMENTS

2004/0225298 A1* 11/2004 Tom ..................... A61B 5/6852
606/108
2014/0276078 A1* 9/2014 Schweitzer ............ A61B 5/283
600/459

(Continued)

FOREIGN PATENT DOCUMENTS

WO    2011022665 A1    2/2011

*Primary Examiner* — Erin M Piateski
(74) *Attorney, Agent, or Firm* — Armstrong Teasdale LLP

(57) ABSTRACT

Aspects of the instant disclosure relate to an elongated medical device. In particular, the instant disclosure relates to apparatuses for sensing contact force. In various embodiments, a force sensing element including a tip and a catheter shaft, wherein the tip is configured to move relative to the shaft when an external force is applied to the tip comprising a transmitter configured to transmit a transmitter signal when external force is applied to the tip, a first plurality of sensors and a second plurality of sensors positioned proximate the transmitter, wherein each of the sensors is configured to receive the transmitter signal and the first plurality of sensors is longitudinally offset from the second plurality of sensors.

29 Claims, 7 Drawing Sheets

(51) Int. Cl.
 *A61M 25/00* (2006.01)
 *A61B 5/287* (2021.01)
 *A61B 18/00* (2006.01)

(52) U.S. Cl.
 CPC ....... *A61B 18/1492* (2013.01); *A61M 25/008* (2013.01); *A61B 2018/00351* (2013.01); *A61B 2018/00577* (2013.01); *A61B 2218/002* (2013.01); *A61B 2562/06* (2013.01); *A61M 2205/332* (2013.01); *A61M 2205/3317* (2013.01)

(58) Field of Classification Search
 CPC .... A61B 2018/00577; A61B 2218/002; A61B 2562/06; A61M 25/008; A61M 2205/3317; A61M 2205/332
 USPC ......................................................... 600/587
 See application file for complete search history.

(56) References Cited

U.S. PATENT DOCUMENTS

2014/0364848 A1* 12/2014 Heimbecher ...... A61B 18/1206
606/41
2016/0076953 A1 3/2016 Cui et al.

\* cited by examiner

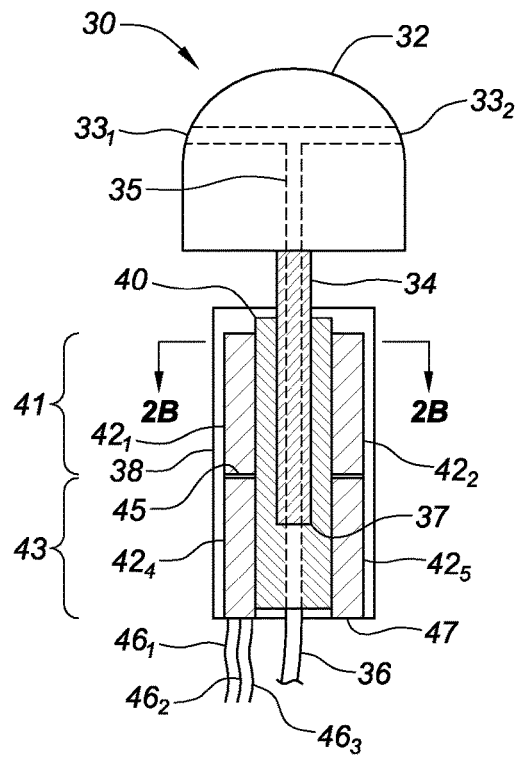
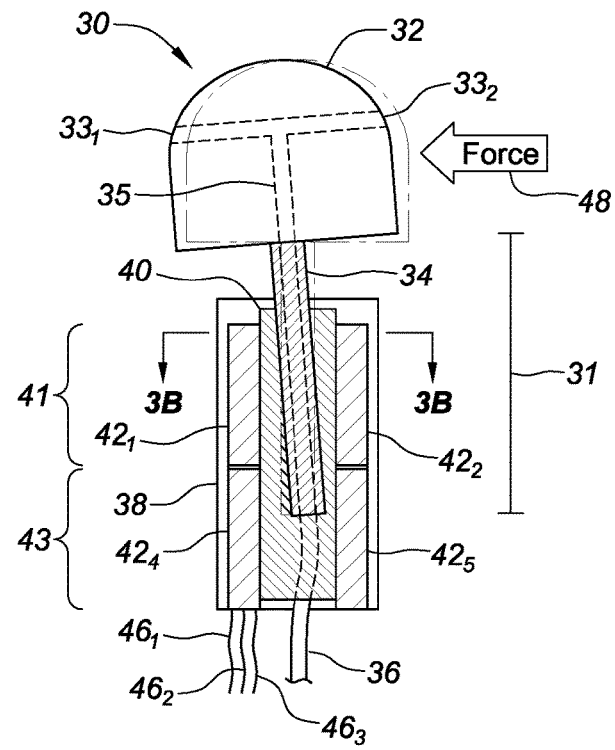
FIG. 2A    FIG. 3A
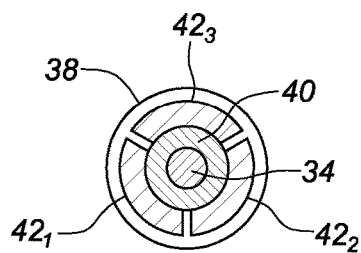
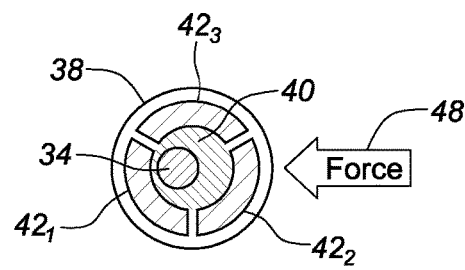
FIG. 2B    FIG. 3B

APPARATUSES, METHODS, AND SYSTEMS FOR CONTACT FORCE SENSING

CROSS-REFERENCE TO RELATED APPLICATIONS

This application claims the benefit of U.S. provisional application No. 62/469,572, filed 10 Mar. 2017, which is hereby incorporated by reference as though fully set forth here.

BACKGROUND a. Field

This disclosure relates to an elongated medical device. In particular, the instant disclosure relates to apparatuses for sensing contact force.

b. Background Art

Electrophysiology catheters are used in a variety of diagnostic and/or therapeutic medical procedures to address conditions such as atrial arrhythmia, including for example, ectopic atrial tachycardia, atrial fibrillation, and atrial flutter. Arrhythmias can create a variety of dangerous conditions including stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other purposes. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. Such treatment requires precise control of the catheter during manipulation to and at the treatment site, which can invariably be a function of a user's skill level.

In the case of an electrophysiological mapping catheter, electrode-to-tissue contact facilitates meaningful capture of electrograms and accurate mapping of the heart. In the case of ablation catheters, sufficient contact may be required for effective formation of lesions in the tissue. A variety of mechanisms and techniques have been employed to determine contact between catheters and tissue, but these are often non-specific and difficult to interpret or require additional components that increase the cost, size, and complexity of the catheter.

BRIEF SUMMARY

The instant disclosure, in at least one embodiment, relates an elongated medical device. The elongated medical device including a tip and a catheter shaft, where the tip is configured to move relative to the shaft when an external force is applied to the tip comprising a transmitter configured to transmit a transmitter signal when external force is applied to the tip, a first plurality of sensors and a second plurality of sensors positioned proximate the transmitter, wherein each of the sensors is configured to receive the transmitter signal and the first plurality of sensors is longitudinally offset from the second plurality of sensors.

In another embodiment, an elongated medical device can include a force sensing element comprising a transmitter plate configured to transmit a transmitter signal when external force is applied to the force sensing element, and a plurality of sensors, wherein the plurality of sensors are mounted to the exterior of the elongated medical device proximate to a distal end of the elongated medical device, wherein each of the plurality of sensors is configured to receive the transmitter signal when an external force is applied to the force sensing element.

In yet another embodiment, a system can comprise a plurality of force sensing elements, each of the plurality of force sensors comprising a transmitter plate configured to transmit a transmitter signal when external force is applied to the force sensing element, and a plurality of sensors, wherein the plurality of sensors are mounted to the exterior of the elongated medical device proximate to a distal end of the elongated medical device, wherein each of the plurality of sensors is configured to receive the transmitter signal when an external force is applied to the force sensing element, and an electronic control unit (ECU), wherein the ECU is configured to receive sensor signals measuring a force exerted by tissue on each of the plurality of sensors for each of the plurality of force sensors.

BRIEF DESCRIPTION OF THE DRAWINGS

FIG. 2A is a side view of a contact force sensing element with a tip connected to a tip element, consistent with embodiments in the present disclosure.

FIG. 2B is a top cross-sectional view of the contact force sensing element of FIG. 2A with the tip connected to the tip element, consistent with embodiments in the present disclosure.

FIG. 3A is a side view the contact force sensing element of FIG. 2A when an exemplary lateral force is applied to the tip causing a tip element to exert a force that can be detected by a plurality of sensors, consistent with embodiments in the present disclosure.

FIG. 3B a top cross-sectional view of the contact force sensing element of FIG. 3A when the exemplary lateral force is applied to the tip causing the tip element to move into the deformable filler material and further causing a change in distance between the tip element and the plurality of sensors, consistent with embodiments in the present disclosure.

DETAILED DESCRIPTION OF EMBODIMENTS

Figure 1:
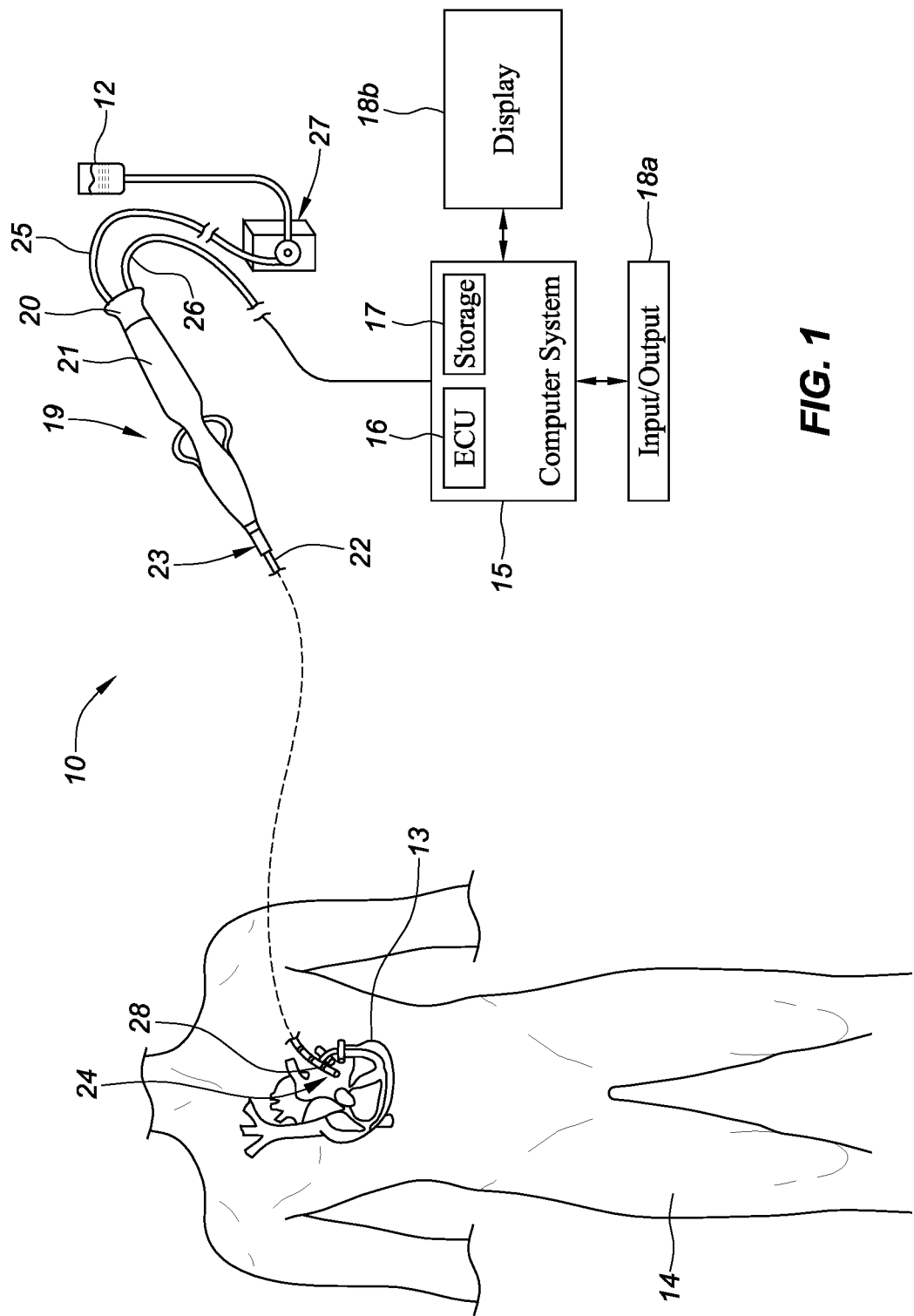
FIG. 1 is an exemplary system diagram of a catheter inserted into a body (the heart), an irrigation system, a computer system with an input/output and display devices.

With reference to FIG. 1, a system 10 can include a medical device 19 and a computer system 15, an input/output device 18a, and a display 18b. The computer system 15 can include an electronic control unit (ECU) 16 and a data storage device 17 (e.g., memory). The medical device 19 can include an elongated medical device such as, for example and without limitation, a catheter, or a sheath, introducer, endoscope, or other device configured for insertion into the body. For purposes of illustration and clarity, the description below will be limited to an embodiment wherein the medical device 19 comprises a catheter (a sample catheter is shown in FIG. 1 (e.g., catheter 19). It will be appreciated, however, that the present disclosure is not meant to be limited to catheters.

With continued reference to FIG. 1, in this exemplary embodiment the catheter 19 can be configured to be inserted into a patient's body 14, and more particularly, into chambers of the patient's heart, with heart tissue 13. The catheter 19 may include a cable connector or interface 20, handle 21 that has a proximal end portion 23, a tubular body or shaft 22 having and a distal end portion 24, and one or more sensors 28 mounted in or on the tubular body 22 of the catheter 19. The catheter 19 may further include other conventional components such as, for example and without limitation, a temperature sensor, additional sensors or electrodes, ablation elements (e.g., ablation tip electrodes for delivering radio frequency (RF) ablative energy, high intensity focused ultrasound ablation elements, etc.), and corresponding conductors or leads. The cable connector 20 may provide mechanical, fluid, and/or electrical connections for cables 25 and 26 extending from a pump 27 to a fluid reservoir 12 and the computer system 15, respectively. The cable connector 20 may comprise conventional components and, as shown, may be disposed at the proximal end of the catheter 19.

The handle 21 provides a portion for a user to grasp or hold the catheter 19 and may further provide a mechanism for steering or guiding the tubular body 22 within the patient's body 14. For example, the handle 21 may include a mechanism configured to change the tension on a pull wire extending through the catheter 19 to the distal end portion 24 of tubular body 22 or some other mechanism to steer the tubular body 22. The handle 21 may be conventional in the art, and it will be understood that the configuration of the handle 21 may vary. In an embodiment, the handle 21 may be configured to provide visual, auditory, tactile and/or other feedback to a user based on information received from the contact force sensing element at the distal end portion 24. For example, if contact to the tissue 13 is made by the contact force sensing element (shown in FIG. 1) at the distal end portion 24, the handle 21 may include a plurality of light-emitting diodes, a tone generator, a vibrating mechanical transducer, and/or other indicator(s), the outputs of which could vary in proportion to the signal sensed at the contact force sensing element at the distal end portion 24.

The tubular body 22 can be an elongated, tubular, flexible member configured for movement within the body 14. The tubular body 22 supports, for example and without limitation, sensors and/or electrodes mounted thereon, such as, for example, sensors, associated conductors, and possibly additional electronics used for signal processing and conditioning. The tubular body 22 may also permit transport, delivery, and/or removal of fluids (including irrigation fluids, cryogenic ablation fluids, and bodily fluids), medicines, and/or surgical tools or instruments. The tubular body may be made from conventional materials such as polyurethane, Pebax® or other suitable polymer, and may define one or more lumens configured to house and/or transport electrical conductors, fluids, or surgical tools. The tubular body may be introduced into a blood vessel or other structure within the body 14 through a conventional introducer. The tubular body may then be steered or guided through the body 14 to a desired location, such as the heart tissue 13.

For purposes of clarity and illustration, the description below will be with respect to an embodiment wherein a single sensor of the catheter 19 comprises a contact force sensing element. It will be appreciated, however, that in other exemplary embodiments, which remain within the spirit and scope of the present disclosure, the catheter 19 may comprise more than one contact force sensing element as well as other sensors or electrodes configured to perform other diagnostic and/or therapeutic functions. As will be described in greater detail below, the contact force sensing element can include a plurality of leads, extending from a sensing element thereof (e.g., a coil), that are configured to electrically couple the contact force sensing element to other components of the system 10, such as, for example, the computer system 15. In some embodiments, the ECU can include a mapping system for generating maps and models of the body 14 (e.g., the heart tissue 13).

FIG. 2A is a side view of a contact force sensing element with a tip connected to a tip element, consistent with embodiments in the present disclosure. The contact force sensing element 30 can include the tip 32 and a tip element 34 where the tip 32 is coupled with the tip element 34. In some embodiments, the tip 32 and the tip element 34 can be combined into the same element. In other embodiments, the tip 32 and the tip element 34 are separate elements that can be connected (e.g., mechanically secured with a chemical bond, etc.) The tip 32 can be, for example, an irrigated RF ablation tip. The irrigated RF ablation tip can be connected to an irrigation lumen 36. The tip element 34 can be enclosed inside a housing 38. The irrigation lumen 36 can be connected to an irrigation source 12 (e.g., a fluid reservoir) (shown in FIG. 1).

The tip element 34 can be surrounded by a deformable filler material 40. The tip element 34 can be any suitable material including, for example, a metal or a polymer (conductive or non-conductive). If the tip element 34 is a non-conductive material, the tip element 34 can be coated with a conductive material. The tip element 34 can be designed so that forces exerted on the tip element 34 during use do not cause flexing or bending of the tip element 34 (e.g., all forces on the tip 32 are translated to movement of the tip element 34 and no force is lost to deflection of the tip element 34). The tip element 34 can be electrically connected to the ECU 16.

The deformable filler material 40 can be a single continuous piece (e.g., a tube) or it can be a plurality of pieces. The deformable filler material can be a dielectric or conductive material which can be deformed when a force is exerted on tip element 34, causing the tip element 34 to deform the deformable filler material 40. For example, the filler material 40 could be a silicone or other medical grade elastomer. The filler material 40 could also be air or some other fluid and/or gas. The filler material 40 can be in contact with a plurality of sensors $42_{1-6}$.

The plurality of sensors can be arranged where there is a first row (or first plurality) of sensors 41 and a second row (or second plurality) of sensors 43. In one embodiment, there can be six sensors, $42_1$, $42_2$ and $42_3$ (in the first plurality of sensors 41) and $42_4$, $42_5$, and $42_6$ (in the second plurality of sensors 43) as shown in FIG. 2A where the second plurality of sensors 43 is longitudinally offset from the first plurality of sensors. For example, the plurality of sensors $42_{1-6}$ can be electrically connected to the computer system 15 (shown in FIG. 1) by wires $46_{1-6}$ where each sensor has a corresponding wire. For example, the sensor $42_1$ can be connected to the computer system 15 by the wire $46_1$. The plurality of sensors $42_{1-6}$ can be arranged to fit in a space between the deformable filler material 40 and a wall of the housing 38. The plurality of sensors $42_{1-6}$ can measure a change in capacitance and/or a change in resistance between the two conductive surfaces (the tip element 34 and the plurality of sensors $42_{1-6}$). In some embodiments, the plurality of sensors $42_{1-6}$ can be, for example, coupled with an exterior of a catheter shaft (not shown) and the deformable filler material can be located either inside or outside of the catheter shaft.

The housing 38 can be configured to attach to the end of the catheter 19 (e.g., using a threaded or mechanical connection or a bonded connection such as a chemical bond) or the housing 38 can be incorporated into a distal end of the catheter 19 (e.g., the housing 38 is integral to the catheter 19). The housing 38 can be any suitable material, including a polymer or a metal (e.g., stainless steel or titanium). The housing 38 can be designed so the material and dimensions (e.g., wall thickness) allow the housing 38 to be rigid enough to prevent bending or deflection under forces typically experienced during use. The rigidity of the housing 38 will limit or eliminate erroneous tissue contact readings related to the housing 38 bending during use of the contact force sensing element 30.

The tip 32 can be attached to the tip element 34 by any suitable means including, for example, adhesive, mechanical connection, friction, welding, or other coupling methods. In one embodiment, the tip 32 and the tip element 34 are incorporated into the same piece of material (e.g., injection molded or machined from a single piece of material). The combination of the tip 32 and the tip element 34 (either as two elements coupled with each other or a single element as described above) can be referred to as the tip. The tip 32 can include a plurality of openings $33_{1-2}$ for irrigation. The plurality of openings $33_{1-2}$ on the tip 32 can be connected to the irrigation lumen 36 through a channel 35 in the tip 32 and the tip element 34.

In some embodiments, the plurality of sensors $42_{1-6}$ can be, for example, coupled with an exterior of a catheter shaft (not shown). The deformable filler material can be located either inside or outside of the catheter shaft.

FIG. 2B is a top cross-sectional view of the contact force sensing element of FIG. 2A with the tip connected to the tip element, consistent with embodiments in the present disclosure. In this view (at the location of line 2B of FIG. 2A), the tip element 34 is in the center of the contact force sensing element 30. The tip element 34 can be a transmitter. For example, the tip element 34 can transmit a signal, a transmitter signal, (e.g., sound, light) or a field (e.g., electrical, magnetic). The signal or field can emit radially (perpendicular to the axis of the tip element 34) or other directions from the tip element 34. The deformable filler material 40 can be proximate the tip element 34. The deformable filler material 40 can be a single piece (e.g., a tube) that completely surrounds the tip element 34. In another embodiment, the deformable filler material 40 can be a plurality of pieces (e.g., donuts or cylinders stacked on top of each other). In some embodiments, the deformable filler material 40 can be cast or molded into a plurality of pieces. In other embodiments, the deformable filler material 40 can be formed using chemical vapor deposition (CVD) or similar processes.

The tip element 34 can have a length 31 (shown in FIG. 3A), long enough to permit a transfer of the force 48 to the plurality of sensors $42_{1-6}$ (e.g., the first plurality of sensors 41 and the second plurality of sensors 43 in FIG. 2A). The length 31 of the tip element 34 can be, for example, configured so that a proximal end 37 of the tip element 34 does not reach a proximal end 47 of the second row of sensors 43.

In another embodiment (not shown) of a contact force sensing element, a shorter tip element attached to the tip 32 can be a shorter length than the length 31 (shown in the embodiment of FIGS. 2A and 2B) and a plurality of sensors $42_{1-3}$ (e.g., a first plurality of sensors 41, only one row of sensors rather than two). The shorter length of the tip element can be such that a proximal end of the tip element does not reach a proximal end 45 of the first row of sensors 41. In yet another embodiment, the contact force sensing element can have additional rows of sensors (e.g., a third row ($42_{7-9}$), a fourth row ($42_{10-12}$), etc.) and the tip element attached to the tip 32 can be longer to facilitate interaction (e.g., via a signal) between the tip element and the sensors.

FIG. 3A is a side view the contact force sensing element of FIG. 2A when an exemplary lateral force is applied to the tip causing the tip element to exert a force that can be detected by the plurality of sensors, consistent with embodiments in the present disclosure. In one embodiment, as the tip 32 is moved by a force 48, the tip 32 also moves the tip element 34 which causes the deformable filler material 40 to deform, which in turn changes the distance between the tip element 34 and the plurality of sensors $42_{1-6}$ (e.g., the tip element 34 moves closer to some sensors and further away from other sensors). The tip 32 moves in the same direction of the force 48.

As described above, the plurality of sensors $42_{1-6}$ can measure, for example, a change in capacitance and/or a change in resistance between the two conductive surfaces (e.g., the tip element 34 and each of the plurality of sensors $42_{1-6}$). In other embodiments, the plurality of sensors $42_{1-6}$ can measure a change in another parameter, such as a light path. The changes in capacitance and/or resistance can generate a signal (e.g., a voltage, a resistance, a capacitance, etc.) from each of the plurality of sensors $42_{1-6}$ that can indicate, for example, a position of the tip 32 and/or tip element 34. The plurality of sensors $42_{1-6}$ are electrically connected to the computer system 15 by a plurality of wires $46_{1-6}$ (e.g., $42_{1-3}$ are electrically connected to the computer system 15 by a plurality of wires $46_{1-3}$) which can record data and allow evaluation by the ECU 17.

The direction in which the force 48 is applied about the circumference of the tip 32 results in a relative change in the separation between the plurality of sensors $42_{1-6}$ and the tip element 34. The ratio of the change in magnitude of the capacitance/resistance between the plurality of sensors $42_{1-6}$ can be used to determine the direction and magnitude of the force 48 applied to the tip 32. As the number of sensors placed about the circumference of the housing 38 increases, the resolution of the direction of the force 48 applied also increases.

The capacitance/resistance of each sensor $42_{1-6}$ can be determined by actively monitoring the difference between an incident signal at the tip electrode 32 during monitoring and/or ablation versus a returned signal through the individual sensors $42_{1-6}$. In the case of a capacitive sensing element, there can be a change in the relationship between the amplitude and phase of the incident signal and the returned signal. In the case of a resistive sensor there can be a change in the relationship between the amplitude of the incident signal and the returned signal. In other embodiments, the plurality of sensors $42_{1-6}$ can measure a change in another parameter, such as a light path. The plurality of sensors $42_{1-6}$ can be electrically connected to the computer system 15 by a plurality of wires $46_{1-6}$ (e.g., $42_{1-3}$ are electrically connected to the computer system 15 by a plurality of wires $46_{1-3}$) which can, for example, record data and allow evaluation by the ECU 17.

FIG. 3B is a top cross-sectional view of the contact force sensing element of FIG. 3A when the exemplary lateral force is applied to the tip, causing the tip element to move into the deformable filler material, thereby causing a change in distance between the tip element and the plurality of sensors, consistent with embodiments in the present disclosure. The contact force sensing element 30 can have an exemplary lateral force 48 applied to the tip 32, causing the tip element 34 to move into the deformable filler material 40, which causes a change in the distance between the tip element 34 and the plurality of sensors $42_{1-6}$. In this view (at the location of line 3B of FIG. 3A), the tip element 34 (at its closest point) is closer to sensor $42_1$ and sensor $42_3$ and further away from sensor $42_2$.

Figure 4A:
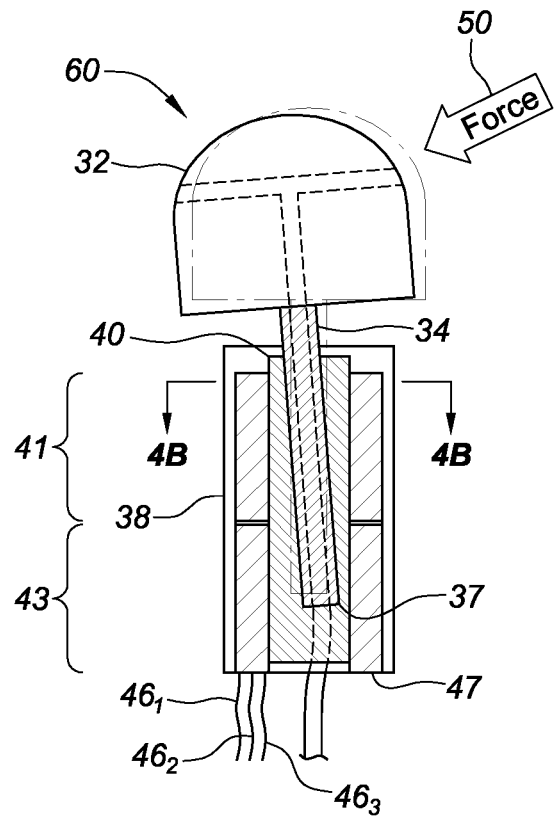
FIG. 4A is a side view of a contact force sensing element when an exemplary front-lateral force is applied to the tip, causing the tip element to move into the deformable filler material, thereby causing a change in distance between the shaft and the plurality of sensors, consistent with embodiments in the present disclosure.

FIG. 4A is a side view of a contact force sensing element when an exemplary front-lateral force is applied to the tip, causing the tip element to move into the deformable filler material, thereby causing a change in distance between the shaft and the plurality of sensors, consistent with embodiments in the present disclosure. In this embodiment, the contact force sensing element 30 can have an exemplary front-lateral force 50 applied to the tip 32, causing the tip element 34 to move into the deformable filler material 40, thereby causing a change in distance between the tip element 34 and the plurality of sensors $42_{1-6}$.

The capacitance/resistance of each sensor $42_{1-6}$ can be determined by actively monitoring the difference between an incident signal at the tip electrode 32 during monitoring and/or ablation versus a returned signal through the individual sensors $42_{1-6}$. In the case of a capacitive sensing element, there can be a change in the relationship between the amplitude and phase of the incident signal and the returned signal. In the case of a resistive sensor there can be a change in the relationship between the amplitude of the incident signal and the returned signal.

Figure 4B:
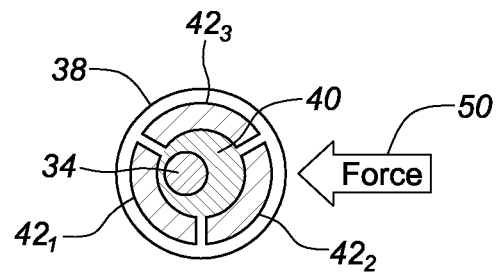
FIG. 4B is a top cross-sectional view of the contact force sensing element 30 of FIG. 4A. when an exemplary front-lateral force is applied to the tip, causing the tip element to move into the deformable filler material causing a change in distance between the shaft and the plurality of sensors, consistent with embodiments in the present disclosure.

FIG. 4B is a top cross-sectional view of the contact force sensing element 30 of FIG. 4A. when an exemplary front-lateral force is applied to the tip, causing the tip element to move into the deformable filler material causing a change in distance between the tip element and the plurality of sensors, consistent with embodiments in the present disclosure. In this embodiment, the contact force sensing element 30 can have an exemplary front-lateral force 50 applied to the tip 32, causing the tip element 34 to move into the deformable filler material 40 causing a change in distance between the tip element 34 and the plurality of sensors $42_{1-6}$. In this view (at location of line 4B of FIG. 4A), the tip element 34 (at its closest point) is closer to sensor $42_1$ and sensor $42_3$ and further away from sensor $42_2$.

Figure 5B:
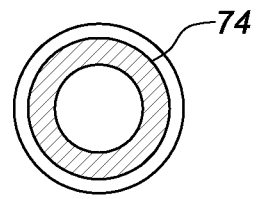
FIGS. 5B-D are top cross-sectional views of the contact force sensing element from FIG. 5A showing a transmitter plate (FIG. 5B), a capacitive/resistive material (FIG. 5C), and sensors (FIG. 5D), consistent with embodiments in the present disclosure.
Figure 5A:
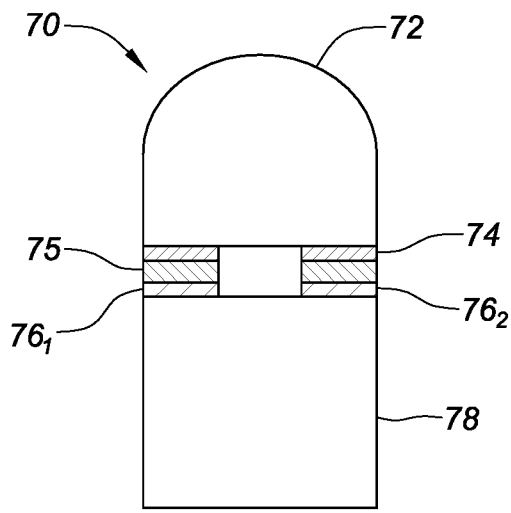
FIG. 5A is a side view of a contact force sensing element which includes a tip electrode, a transmitter plate, a compressible capacitive/resistive material, a plurality of sensors, and a housing, consistent with embodiments in the present disclosure.

FIG. 5A is a side view of a contact force sensing element which includes a tip electrode, a transmitter plate, a compressible capacitive/resistive material, a plurality of sensors, and a housing, consistent with embodiments in the present disclosure. The contact force sensing element 70 can be arranged as shown in FIG. 5A with the tip electrode 72, the transmission plate 74, the compressible capacitive/resistive material 75, a plurality of sensors $76_{1-3}$ and the housing 78, where the compressible capacitive/resistive material 75 can be between the transmission plate 74 and the plurality of sensors $76_{1-3}$. In some embodiments, the tip 72 can act as a transmitter and the transmission plate 74 may not be needed.

Referring to FIG. 5A, the capacitance/resistance of each sensor $76_{1-3}$ can be determined by actively monitoring the difference between an incident signal at the tip electrode 72 during monitoring and/or ablation versus a returned signal through the individual sensors $76_{1-3}$. In the case of a capacitive sensing element, there can be a change in the relationship between the amplitude and phase of the incident signal and the returned signal. In the case of a resistive sensor there can be a change in the relationship between the amplitude of the incident signal and the returned signal.

The compressible capacitive/resistive material 75, the sensor transmitter plate 74 and the plurality of sensors $76_{1-3}$ are arranged as shown. The compressible capacitive/resistive material 75 can be in between the transmitter plate 74 and the plurality of sensors $76_{1-3}$. The transmitter plate 74, which can be electrically connected to the tip electrode 72, can provide the incident signal (e.g., a voltage) from the monitoring/ablation equipment. The plurality of sensors $76_{1-3}$ can be attached to the compressible capacitive/resistive material 75 and can also be attached to the top of the housing 78 to form an integrated sensor. The plurality of sensors $76_{1-3}$ can be configured to receive a signal (e.g., a voltage). As described above, the change in thickness of the compressible/stretchable capacitive/resistive material, due to an applied external force, results in a change in the capacitance/resistance between the two conductive surfaces of the transmitter plate 74 and the plurality of sensors $76_{1-3}$. The transmitter plate 74 and the plurality of sensors $76_{1-3}$ can be electrically connected to the computer system 15 which can monitor/record the change in resistance/capacitance and allow evaluation by the ECU 17.

Figure 5C:
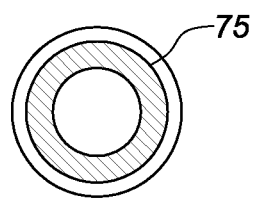
Figure 5D:
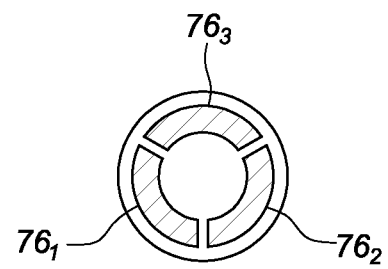

FIGS. 5B-D are top cross-sectional views of the contact force sensing element from FIG. 5A showing a transmitter plate (FIG. 5B), a capacitive/resistive material (FIG. 5C), and sensors (FIG. 5D), consistent with embodiments in the present disclosure. The capacitive/resistive material 75 can also be, for example, a dielectric or conductive material. The capacitive/resistive material 75 can be in between the transmitter plate 74 and the sensors 76.

Referring to FIG. 5B, in other embodiments, the transmitter plate 74 can be separated into multiple transmitter plates (e.g., $74_1$, $74_2$, $74_3$, similar to the configuration shown in FIG. 5D). The transmitter plates can be any suitable dimensions. The greater the number of transmitter plates, the better a resolution of directionality of a force on the tip 72. The transmitter plates can be electrically connected to the computer system 15 which can monitor/record the change in resistance/capacitance and allow evaluation by the ECU 17.

Referring to FIG. 5C, similar to the discussion above regarding FIG. 5B, the capacitive/resistive material 75 can be a single piece of material or multiple pieces.

Referring to FIG. 5D, an exemplary embodiment is shown with three sensors $76_{1-3}$. Additional sensors can be included (e.g., $76_{1-10}$) with each sensor being a smaller size. As with an embodiment with multiple transmitter plates 74, a larger number of sensors $76_{1-3}$ can permit a greater resolution of directionality of a force on the tip 72.

Figure 5E:
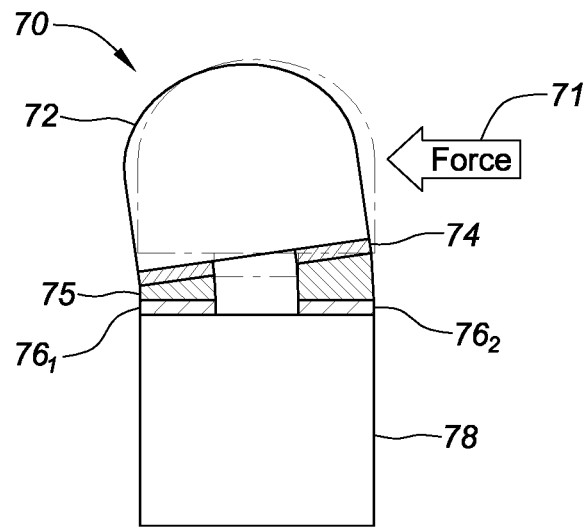
FIG. 5E is a side view of the contact force sensing element of FIG. 5A when an exemplary lateral force is applied to the tip causing a proximal surface (and transmitter plate) of the tip to move closer to one of the sensors and further away from another sensor, consistent with embodiments in the present disclosure.

FIG. 5E is a side view of the contact force sensing element of FIG. 5A when an exemplary lateral force is applied to the tip causing a proximal surface (and transmitter plate) of the tip to move closer to one of the sensors and further away from another sensor, consistent with embodiments in the present disclosure. FIG. 5E show the contact force sensing element 70 of FIG. 5A when an exemplary lateral force 71 is applied to the tip 72 causing a proximal surface 73 (and transmitter plate 74) of the tip 72 to move closer to one of the sensors $76_1$ and further away from another sensor $76_2$. The change in distance between the tip 72 and each of the transmitter plates 74 creates a change in the signal received by the plurality of sensors $76_{1-3}$.

As discussed above with respect to FIG. 5A, the capacitance/resistance of each sensor $76_{1-3}$ (only sensors $76_{1-2}$ are shown in FIG. 5E) can be determined by actively monitoring the difference between an incident signal at the tip electrode 72 during monitoring and/or ablation versus a returned signal through the individual sensors $76_{1-3}$. In the case of a capacitive sensing element, there can be a change in the relationship between the amplitude and phase of the incident signal and the returned signal. In the case of a resistive sensor there can be a change in the relationship between the amplitude of the incident signal and the returned signal.

Figure 5F:
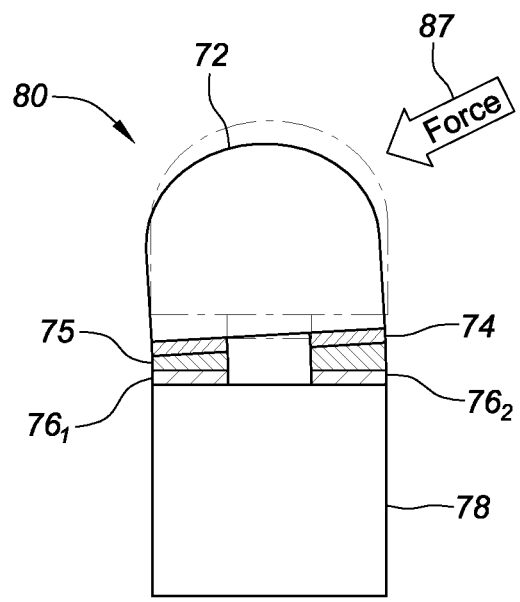
FIG. 5F is a side view of a contact force sensing element of FIG. 5A when an exemplary front-lateral force is applied to the tip, causing a proximal surface of the tip to exert a force that causes a transmitter plate to send a signal that can be detected by a sensor, consistent with embodiments in the present disclosure.

FIG. 5F is a side view of a contact force sensing element of FIG. 5A when an exemplary front-lateral force is applied to the tip, causing a proximal surface of the tip to exert a force that causes a transmitter plate to send a signal that can be detected by a sensor, consistent with embodiments in the present disclosure. In this embodiment, when the tip 72 is pushed toward the housing 78 by an exemplary front-lateral force 87, the transmitter plate 74 can come in closer proximity to all of the plurality of sensors $76_{1-3}$ (compared to the embodiment in FIG. 5E with only a lateral force) in addition to change in distance described for the embodiment shown in FIG. 5E (only a lateral force on the tip 72).

Figure 6A:
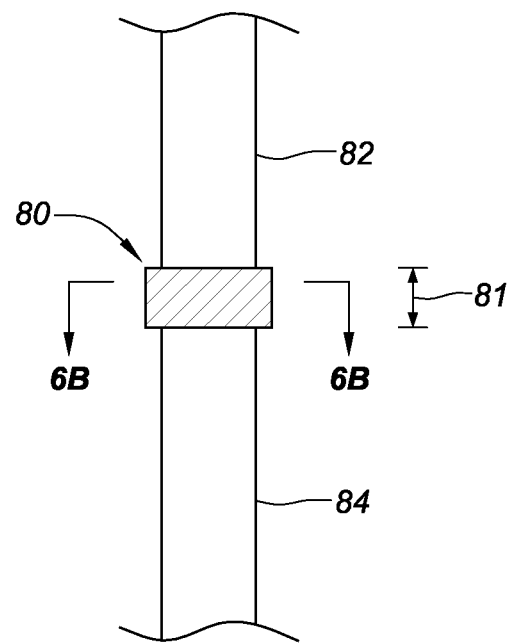
FIG. 6A is a side view of a contact force sensing element coupled with an elongated medical device, consistent with embodiments in the present disclosure.

FIG. 6A is a side view of a contact force sensing element coupled with an elongated medical device, consistent with embodiments in the present disclosure. The contact force sensing element 80 can be coupled with the elongated medical device 82. The elongated medical device 82 can be flexible, where a distal end of the flexible medical device can be formed in various configurations (discussed in further detail below). The contact force sensing element can be coupled with the elongated medical device 82 at any suitable location. One or more contact force sensing elements can be used.

Figure 6B:
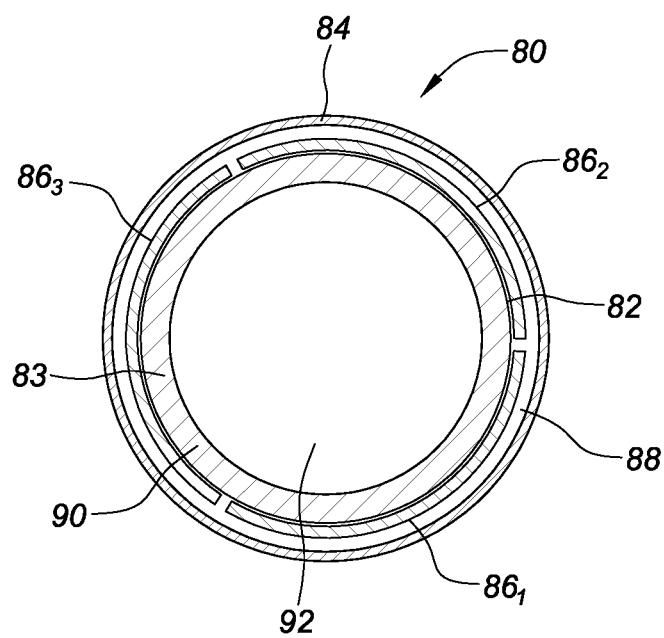
FIG. 6B is a top cross-sectional view of the contact force sensing element from FIG. 6A (in the location of line 6B in FIG. 6A), consistent with embodiments in the present disclosure.

FIG. 6B is a top cross-sectional view of the contact force sensing element from FIG. 6A (in the location of line 6B in FIG. 6A), consistent with embodiments in the present disclosure. The contact force sensing element 80 can include an electrode 84, sensors $86_{1-3}$, and a deformable filler material 88. The elongated medical device 82 can include a tubular shaft 90 and a lumen 92. The tubular shaft 90 can have a wall thickness of any suitable amount. The lumen 92 can include one or more lumens.

The capacitance/resistance of each sensor $86_{1-3}$ can be determined by actively monitoring the difference between an incident signal at the tip electrode 84 (e.g., a transmitter, or a transmitter plate) during monitoring and/or ablation versus a returned signal through the individual sensors $86_{1-3}$. In the case of a capacitive sensing element, there can be a change in the relationship between the amplitude and phase of the incident signal and the returned signal. In the case of a resistive sensor there can be a change in the relationship between the amplitude of the incident signal and the returned signal. The contact force sensing element 80 can be electrically connected to the computer system 15 which can record data and allow evaluation by the ECU 16.

In some embodiments, the contact force sensing element 80 can be coupled with an elongated medical device 82. The contact force sensing element 80 can be, for example, coupled with an exterior wall of the elongated medical device 82. The force sensing element 80 can include a deformable filler material 88 that can be, for example, a dielectric or conductive material which can be deformed, for example, when a force is exerted on the elongated medical device 82 causing the exterior wall of the elongated medical device 82 to deform the deformable filler material 88. In other embodiments, the electrode 84 can cause the deformable filler material 88 to deform when a force is exerted on the electrode 84. The force sensing element 80 can also include a plurality of sensors $86_{1-3}$. The plurality of sensors $86_{1-3}$ can detect a signal (e.g., a voltage) from the electrode 84.

Figure 7A:
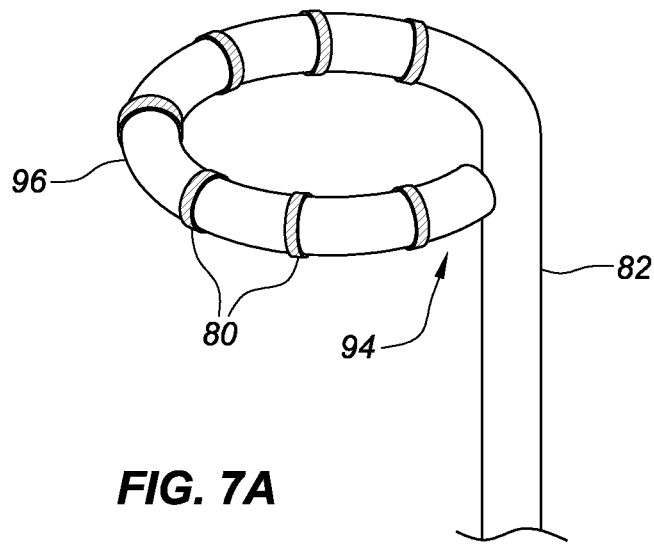
FIG. 7A is a side and top view of the contact force sensing element of FIGS. 6A and 6B on an elongated medical device, consistent with embodiments in the present disclosure.

FIG. 7A is a side and top view of the contact force sensing element of FIGS. 6A and 6B on an elongated medical device, consistent with embodiments in the present disclosure. The contact force sensing element 80 can be mounted at any suitable location of the distal end portion 24 of catheter 19 including. For example, a plurality of contact force sensing elements 80 can be coupled with the elongated medical device 82, where a distal end 94 of the elongated medical device 82 can be configured in the shape of a hoop 96. The hoop 96 can be shaped to fit a specific body feature (e.g., the pulmonary vein (PV)). In some embodiments the elongated medical device 82 can be used for PV isolation (PVI) during ablation procedures. The contact force sensing element 80 can be mounted to the exterior wall of the elongated medical device 82 similar to the description above for FIG. 6B. The contact force sensing element 80 can be used to detect the contact force exerted on, for example, the contact force sensors and/or portions of the hoop 96 by tissue. The detected contact forces can be used to, for example, facilitate contact between the PV and the hoop 96.

Figure 7B:
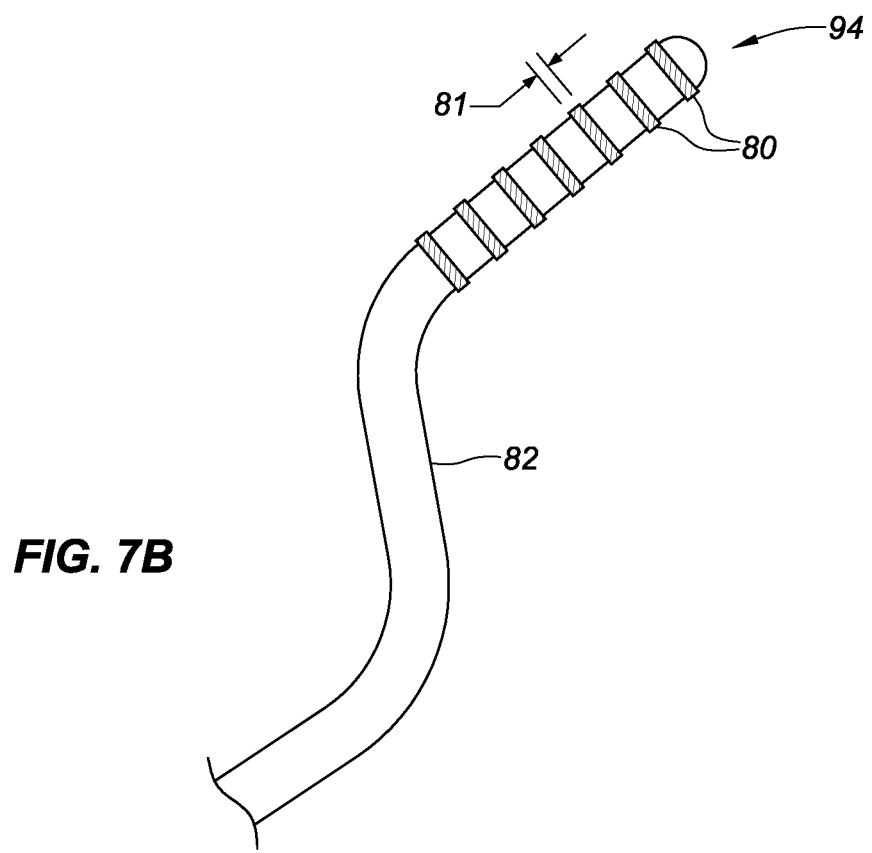
FIG. 7B is a side view of a contact force sensing element of FIGS. 6A and 6B on an elongated medical device with a section of a distal end for linear sensing/detecting and therapy.

FIG. 7B is a side view of a contact force sensing element of FIGS. 6A and 6B on an elongated medical device with a section of a distal end for linear sensing/detecting and therapy, consistent with embodiments in the present disclosure. The plurality of contact force sensing elements 80 can have a width 81 and can be mounted on, for example, an elongated medical device 82. In one embodiment, the elongated medical device 82 can be a flexible catheter. The distal end 94 of the elongated medical device 82 can be, for example, configured to form a linear configuration of the plurality of contact force sensing elements 80. The linear configuration can facilitate contact of the plurality of contact force sensing elements 80 to contact the tissue 13. The plurality of contact force sensing elements 80 can be used, for example, when lines of ablations are created.

The flexible catheter can, for example, conform to variations in the shape/profile of tissue to allow the linear configuration to facilitate contact between the plurality of contact force sensing elements 80 and the tissue. In some embodiments, the plurality of contact force sensing elements 80 can be mounted along a section of the elongated medical device 82 (e.g., at a tip/end location, proximal a distal end, etc.). The contact force sensing elements 80 can have, for example, any suitable distance between the contact force sensing elements. The spacing between the various contact force sensing elements can be any suitable spacing and can be equal or varied spacing. The plurality of contact force sensing elements 80 can be narrower than the embodiment shown in FIGS. 7B (and 6A, 6B, and 7A) to, for example, accommodate a curvature of the hoop 96.

Although at least one embodiment of a force sensing catheter element has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A force sensing element for an elongated medical device including a tip and a catheter shaft, wherein the tip is configured to move relative to the shaft when an external force is applied to the tip, the force sensing element comprising: a transmitter configured to transmit a transmitter signal when external force is applied to the tip; a first plurality of sensors and a second plurality of sensors positioned proximate the transmitter, the first plurality of sensors and the second plurality of sensors concentrically surrounding a deformable filler material, wherein each of the sensors is configured to receive the transmitter signal and the first plurality of sensors is longitudinally offset from the second plurality of sensors.

2. The force sensing element of claim 1, wherein the first and the second plurality of sensors are capacitive sensors.

3. The force sensing element of claim 2, wherein the filler material is a dielectric material, and wherein the transmitter signals, received by the first and the second plurality of sensors, are indicative of a capacitance between the transmitter and each of the respective sensors.

4. The force sensing element of claim 1, wherein the first and the second plurality of sensors are resistive sensors.

5. The force sensing element of claim 4, wherein the filler material is a resistive material, and wherein the transmitter signals, received by the first and the second plurality of sensors, are indicative of a resistance between the transmitter and each of the respective sensors.

6. The force sensing element of claim 4, further comprising a filler material positioned between the transmitter and the first and the second plurality of sensors to form a conductive layer, and wherein the transmitter signals, received by the first and the second plurality of sensors, are indicative of a conductance between the transmitter and each of the respective sensors.

7. The force sensing element of claim 1, wherein the tip further comprises one or more irrigation channels in the tip connected to a plurality of openings on a surface of the tip.

8. The force sensing element of claim 1, further comprising an electronic control unit (ECU), wherein the ECU is configured to receive sensor signals identifying a position of the transmitter relative to each of the first and the second plurality of sensors.

9. The force sensing element of claim 8, wherein the ECU is further configured to measure the external force exerted on the tip, wherein the external force measured comprises a magnitude and a direction.

10. The force sensing element of claim 1, wherein the transmitter is configured to move, in response to the external force applied to the tip, radially relative to the first and the second plurality of sensors, where the radial movement is associated with the external force applied to the tip.

11. The force sensing element of claim 1, wherein the transmitter is configured to move, in response to the external force applied to the tip, longitudinally relative to the first and the second plurality of sensors, where the longitudinal movement is associated with the external force applied to the tip.

12. The force sensing element of claim 1, wherein the first and the second plurality of sensors are configured to receive a modified transmitter signal, wherein the modified transmitter signal is indicative of the external force applied to the tip.

13. The force sensing element of claim 8, wherein the ECU is further configured to determine an axial force based on longitudinal movement of the transmitter with respect to the first and the second plurality of sensors.

14. The force sensing element of claim 8, wherein the ECU is further configured to determine a radial force based on radial movement of the transmitter with respect to the first and the second plurality of sensors.

15. A force sensing element for an elongated medical device comprising a tip and a catheter shaft, the force sensing element comprising: a transmitter plate configured to transmit a transmitter signal when external force is applied to the force sensing element; and a plurality of sensors concentrically encased by a deformable filler material, wherein the plurality of sensors are mounted on an exterior wall of the catheter shaft of the elongated medical device proximate to a distal end of the elongated medical device, wherein each of the plurality of sensors is configured to receive the transmitter signal when an external force is applied to the force sensing element.

16. The force sensing element of claim 15, wherein the plurality of sensors are capacitive sensors.

17. The force sensing element of claim 16, wherein the filler material is a dielectric material, positioned and wherein the transmitter signals, received by the plurality of sensors, are indicative of a capacitance between the transmitter and each of the respective sensors.

18. The force sensing element of claim 15, wherein the plurality of sensors are resistive sensors.

19. The force sensing element of claim 18, wherein the filler material is a resistive material, and wherein the transmitter signals, received by the plurality of sensors, are indicative of a resistance between the transmitter and each of the respective sensors.

20. The force sensing element of claim 18, wherein the filler material is a conductive material, and wherein the transmitter signals, received by the plurality of sensors, are indicative of a conductance between the transmitter and each of the respective sensors.

21. The force sensing element of claim 15, further comprising an electronic control unit (ECU), wherein the ECU is configured to receive sensor signals identifying a force exerted by tissue on each of the plurality of sensors.

22. The force sensing element of claim 17, wherein each of the plurality of sensors surrounds a portion of the elongated medical device.

23. The force sensing element of claim 17, further comprising an electronic control unit (ECU), wherein the ECU is configured to receive sensor signals measuring the force exerted by tissue on the force sensing element.

24. A system, comprising: a plurality of force sensing elements, each of the plurality of force sensing elements comprising: a transmitter plate configured to transmit a transmitter signal when external force is applied to the force sensing element; and a plurality of sensors concentrically encased by a deformable filler material, wherein the plurality of sensors are mounted on an exterior wall of a catheter shaft of an elongated medical device proximate to a distal end of the elongated medical device, wherein each of the plurality of sensors is configured to receive the transmitter signal when an external force is applied to the force sensing element; and an electronic control unit (ECU), wherein the ECU is configured to receive sensor signals measuring a force exerted by tissue on each of the plurality of sensors for each of the plurality of force sensors.

25. The system of claim 24, wherein the plurality of sensors are capacitive sensors.

26. The system of claim 25, wherein the filler material is a dielectric material, and wherein the transmitter signals, received by the plurality of sensors, are indicative of a capacitance between the transmitter and each of the respective sensors.

27. The system of claim 24, wherein the plurality of sensors are resistive sensors.

28. The system of claim 27, wherein the filler material is a resistive material, and wherein the transmitter signals, received by the plurality of sensors, are indicative of a resistance between the transmitter and each of the respective sensors.

29. The system of claim 27, wherein the filler material is a conductive material, and wherein the transmitter signals, received by the plurality of sensors, are indicative of a conductance between the transmitter and each of the respective sensors.

* * * * *

UNITED STATES PATENT AND TRADEMARK OFFICE
CERTIFICATE OF CORRECTION

| | | |
|---|---|---|
| PATENT NO. | : 11,707,231 B2 | Page 1 of 1 |
| APPLICATION NO. | : 16/492208 | |
| DATED | : July 25, 2023 | |
| INVENTOR(S) | : Lupotti et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 906 days.

Signed and Sealed this
Twelfth Day of November, 2024

Katherine Kelly Vidal
*Director of the United States Patent and Trademark Office*